United States Patent [19]

Nohira et al.

[11] Patent Number: 5,021,593
[45] Date of Patent: Jun. 4, 1991

[54] RUTHENIUM-OPTICALLY ACTIVE PHOSPHINE COMPLEX

[75] Inventors: Hiroyuki Nohira, Saitama; Hidemasa Takaya, Shiga; Akira Miyashita, Saitama, all of Japan

[73] Assignee: Takasago International Corporation, Tokyo, Japan

[21] Appl. No.: 551,110

[22] Filed: Jul. 11, 1990

[30] Foreign Application Priority Data

Jul. 11, 1989 [JP] Japan ................................. 1-177257
Mar. 9, 1990 [JP] Japan ................................. 2-58791

[51] Int. Cl.$^5$ ............................................. C07F 15/00
[52] U.S. Cl. ......................................... 556/20; 556/16; 556/136
[58] Field of Search ............................ 556/16, 20, 136

[56] References Cited

U.S. PATENT DOCUMENTS

| 4,400,548 | 8/1983 | Abatjoglou et al. | 556/16 X |
| 4,748,261 | 5/1988 | Billig et al. | 556/136 X |
| 4,904,808 | 2/1990 | Devon et al. | 556/136 X |

*Primary Examiner*—Arthur C. Prescott

*Attorney, Agent, or Firm*—Sughrue, Mion, Zinn, Macpeak & Seas

[57] ABSTRACT

A ruthenium-optically active phosphine complex having, as a ligand, BICHEP which means 2,2'-bis(dicyclohexylphosphino)-6,6'-dimethyl-1,1'-biphenyl represented by formula (I):

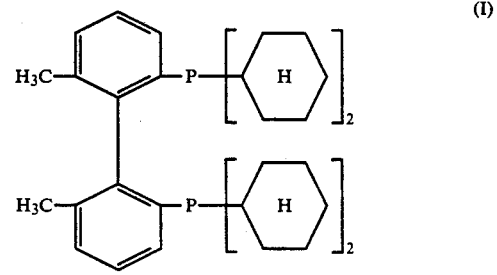

is disclosed, which can catalyze asymmetric syntheses, such as asymmetric hydrogenation, asymmetric isomerization, and asymmetric silylation, exhibiting excellent catalytic activity and providing high optical purity.

6 Claims, No Drawings

RUTHENIUM-OPTICALLY ACTIVE PHOSPHINE COMPLEX

FIELD OF THE INVENTION

This invention relates to a ruthenium-optically active phosphine complex which is useful as a catalyst for various organic syntheses, particularly asymmetric hydrogenation, asymmetric isomerization, and asymmetric silylation.

BACKGROUND OF THE INVENTION

Organic synthesis reactions using metal complexes as catalysts have hitherto been utilized for many purposes. In particular, many reports have been made regarding asymmetric catalysts useful for asymmetric syntheses, such as asymmetric isomerization and asymmetric hydrogenation.

For example, in order to improve the performance of these catalysts, various phosphine compounds having a special structure have hitherto been developed as disclosed, e.g., in Kaqaku Sosetsu, Vol. 32, pp. 237–238, "Yuki Kinzoku Sakutai no Kagaku" (1982), edited by The Chemical Society of Japan and J. D. Morrison, Asymmetric Synthesis, Vol. 5, Academic Press, Inc. (1985). Among them, many complexes in which a chiral tertiary phosphine compound is coordinated to a metal, e.g., rhodium, ruthenium, and palladium, exhibit excellent performance as a catalyst for asymmetric synthesis. In particular, 2,2'-bis(diphenylphosphino)-1,1'-binaphthyl (hereinafter abbreviated as "BINAP") is one of the excellent phosphine compounds as described in JP-A-55-61937 (the term "JP-A" as used herein means an "unexamined published Japanese patent application"). Further, it has also been reported that 2,2'-bis(diphenylphosphino)-6,6'-dimethyl-1,1'-biphenyl (hereinafter abbreviated as "BIPHENP") is an effective catalyst component in asymmetric hydrogenation as described in JP-A-63-135397.

The most commonly employed processes for synthesizing optically active carboxylic acids include a process comprising chemically oxidizing a naturally occurring optically active alcohol or aldehyde to obtain a corresponding carboxylic acid, a process comprising optically resolving a racemic carboxylic acid with an optically active amine, and a process comprising converting a racemic carboxylic acid to its ester and partially hydrolyzing the ester with the aid of an enzyme or a microorganism to obtain a desired carboxylic acid.

In addition, an optically active carboxylic acid can be obtained by asymmetric hydrogenation of an α,β-unsaturated carboxylic acid in the presence of a chiral catalyst. In this case, satisfactory results may be obtained in the syntheses of some carboxylic acids but, in general, the choice of an optically active phosphine as a component of the chiral catalyst is of importance, and there have been developed only few chiral phosphine compounds that are applicable for general purposes.

In an attempt to develop a phosphine compound providing catalysts having excellent catalytic performance, the present inventors conducted extensive investigations on tertiary phosphine compounds having axial chirality. As a result, they found that 2,2'-bis(dicyclohexylphosphino)-6,6'-dimethyl-1,1'-biphenyl (hereinafter referred to as "BICHEP") represented by formula (I):

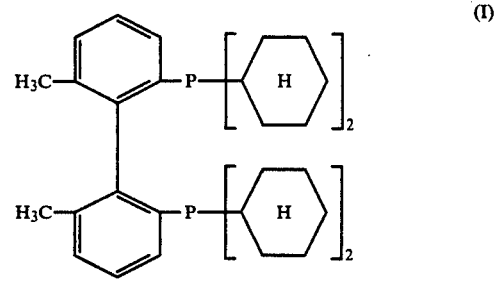

significantly increases stereoselectivity in asymmetric synthesis, i.e., optical yield, as reported in Miyashita, et al., The 58th Springtime Annual Meeting of The Chemical Society of Japan, Lecture Preprint II, pp. 1492 (1989).

SUMMARY OF THE INVENTION

An object of this invention is to provide a rutheniumoptically active phosphine complex having BICHEP as a ligand, which is useful as a catalyst having markedly improve catalytic activity in selectivity, durability, and the like irrespective of the reaction mode and the reaction substrate.

DETAILED DESCRIPTION OF THE INVENTION

BICHEP which is used as a ligand of the complex of the present invention can be synthesized by, e.g., the process reported in Miyashita, et al., The 58th Springtime Annual Meeting of The Chemical Society of Japan, Lecture Preprint II, pp. 1492 (1989).

More specifically, o-toluidine (2) is treated with acetic anhydride to acetylate the amino grou to obtain N-acetyl-o-toluidine (3). The compound (3) is nitrated with nitric acid to obtain 2-acetylamino-3-nitrotoluene (4) which is then hydrolyzed with a hydrochloric acid aqueous solution to obtain 2-amino-3-nitrotoluene (5). The compound (5) is diazotized with sodium nitrite in the presence of sulfuric acid and then treated with an aqueous potassium iodide to obtain crude 2-iodo-3-nitrotoluene (6). The crude product is recrystallized from ethanol to obtain a pale yellow pure compound (6) The compound (6) is allowed to react with stirring at 200° C. for 10 hours in the presence of a copper powder, and the reaction mixture is extracted with benzene using a Soxhlet extractor to obtain 6,6'-dimethyl-2,2'-dinitro-1,1'-biphenyl (7). The compound (7) is hydrogenated in the presence of a Raney nickel W2 type catalyst using hydrazine hydrate as a hydrogen source to obtain crude 6,6'-dimethyl-2,2'-diamino-1,1'-biphenyl (8). After the catalyst is removed, the solvent is removed under reduced pressure to obtain a pale yellow pure compound (8). Subsequently, the compound (8) is dissolved in a 47% hydrobromic acid aqueous solution, and a sodium nitrite aqueous solution is slowly added dropwise thereto under ice-cooling (0° C.), followed by stirring at −5° to −3° C. for 2.5 hours. The resulting solution is added slowly to a separately prepared refluxing solution of cuprous bromide in a 47% hydrobromic acid aqueous solution. After the addition, the mixture is further heated at reflux for 2.5 hours. To the reaction mixture are added methylene chloride and water, the mixture is stirred, and an organic layer is concentrated to obtain a black crude crystal. The crystal is purified twice by means of column chromatography to obtain 6,6'-dimethyl-2,2'-dibromo-1,1'-biphenyl (9) as a white crystal. The compound (9) is dissolved in tetrahydrofuran, the solution is cooled to −78° C., and a hexane solution of t-butyllithium is slowly added dropwise to the cooled solution. After the addition, the temperature is elevated to −45° C., and the reaction is continued for an additional 4 hours. After again cooling to −78° C., a tetrahydrofuran solution of dicyclohexylphosphinic chloride (10) is added to the reaction mixture, followed by allowing to warm to room temperature by spontaneous temperature elevation. The resulting mixture is heated at reflux for 3 hours. The solvent is removed by distillation under reduced pressure, toluene is added to the residue, and the residue is washed successively with a 2N sodium hydroxide aqueous solution and water, followed by concentration. Recrystallization of the concentrate from acetone gives racemic 2,2′-bis(dicyclohexylphosphinyl)-6,6′-dimethyl-1,1′-biphenyl (11) as a white crystal. The racemic compound (11) is dissolved in a mixed solvent of ethyl acetate and chloroform under heating, and a hot ethyl acetate solution of (−)-dibenzoyltartaric acid is added thereto, followed by allowing to stand to precipitate. The precipitated crystal is repeatedly recrystallized until the crystal shows a constant optical rotation The purified crYstal is suspended in toluene, and a 2N sodium hydroxide aqueous solution is added thereto to convert the compound to a free diphosphine oxide (12). Recrystallization from chloroform-ethyl acetate gives pure 2,2′-bis(dicyclohexylphosphinyl)-6,6′-dimethyl-1,1′-biphenyl (12).

Xylene and triethylamine are added to the optically pure 2,2′-bis(dicyclohexylphosphinyl)-6,6′-dimethyl-1,1′biphenyl (12) ($[\alpha]_D^{20}$: −75.3°), and trichlorosilane is added thereto under ice-cooling. The mixture is heated at 120° C. for 2 hours and then at 130° C. for 2 hours, followed by cooling to room temperature. A 30% sodium hydroxide aqueous solution is added thereto to completely dissolve any solid matter, methylene chloride is added, and the mixture is refluxed at 60° C. for 2 hours. An organic layer is separated and dried, and the solvent is removed by distillation. The residue is recrystallized from methanol to obtain a white crystal of BICHEP.

The ruthenium-optically active phosphine complex of the present invention is a ruthenium complex having BICHEP as a ligand and is represented by either one of the following formulae (II), (III), or (IV):

$$[Ru(BICHEP)](OCOR^0)_2 \quad (II)$$

wherein $R^0$ represents a lower alkyl group (preferably containing from 1 to 4 carbon atoms) or a substituted or unsubstituted aryl group (e.g., a phenyl group),

$$[RuXA(BICHEP)]X' \quad (III)$$

wherein X and X′ simultaneously represent the same halogen atom (e.g., an iodine atom, a chlorine atom, a bromine atom); and A represents a substituted or unsubstituted phenyl group, or

$$[Ru_2Cl_4(BICHEP)_2]R^{00} \quad (IV)$$

wherein $R^{00}$ represents a tertiary amine (preferably having lower alkyl groups each containing from 1 to 4 carbon atoms).

The complex of formula (II) can be prepared according to the process disclosed in U.S. Pat. No. 4,739,084; the complex of formula (III) can be prepared according to the process disclosed in European Patent 366,390A; and the complex of formula (IV) can be prepared according to the process disclosed in U.S. Pat. No. 4,691,037, respectively.

Specific but non-limitative examples of the ruthenium-optically active phosphine complex of the present invention are enumerated below.

| | |
|---|---|
| [Ru(BICHEP)](OAc)₂ | (wherein Ac means an acetyl group) |
| [Ru(BICHEP)(p-cymene)I]I | |
| [Ru(BICHEP)(p-cymene)Cl]Cl | |
| [Ru₂Cl₄(BICHEP)₂]NEt₃ | (wherein Et means an ethyl group) |

Among them are preferred [Ru(BICHEP)](OAc)₂ and [Ru(BICHEP)(p-cymene)I]I.

By using as a catalyst the complex according to the present invention, an optically active carboxylic acid or an ester thereof represented by formula (V):

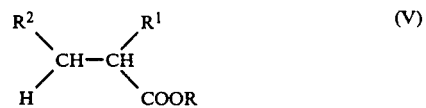

wherein R represents a hydrogen atom or a lower alkyl group (preferably containing from 1 to 4 carbon atoms); $R^1$ represents a lower alkyl group (preferably containing from 1 to 4 carbon atoms), $CH_2COOR^3$ (wherein $R^3$ represents a hydrogen atom or a lower alkyl group (preferably containing from 1 to 4 carbon atoms)), or $NHR^4$ (wherein $R^4$ represents a formyl group, an acetyl group, a benzoyl group, or a chloroacetyl group); and $R^2$ represents a hydrogen atom, a lower alkyl group (preferably containing from 1 to 4 carbon atoms), or a phenyl group, can be produced.

In more detail, an α,β-unsaturated carboxylic acid represented by formula (VI):

wherein R, $R^1$, and $R^2$ are as defined above, the above-described complex catalyst, and a solvent are charged in a pressure reaction vessel under a nitrogen atmosphere, and hydrogen is filled therein to commence a hydrogenation reaction.

The catalyst of the present invention is used in an amount of from 0.02 to 0.0001 mole, preferably from 0.01 to 0.001 mole, per mole of the α,β-unsaturated carboxylic acid.

Generally employed solvents can be used. Examples of suitable solvents are alcohols (e.g., methanol, ethanol, and isopropanol), tetrahydrofuran, benzene, toluene, etc., and mixtures thereof. The solvent is used in an amount of from 0.5 to 20 l per mole of the α,β-unsaturated carboxylic acid.

The hydrogen pressure for reaction usually ranges from 1 to 100 kg/cm² The reaction temperature is from 5° to 70° C., and preferably from 10° to 30° C. The reaction is continued until the pressure is diminished to a prescribed level, and the reaction time usually ranges from 10 minutes to 20 hours, though depending on the reaction time.

After the reaction, the solvent is removed by distillation, and the residue is neutralized. The catalyst is then removed by extraction with chloroform, carbon tetrachloride, dichloromethane, etc. The residue is again rendered acidic with a mineral acid and then extracted with diethyl ether, chloroform, dichloromethane, benzene, toluene, ethyl acetate, etc. to obtain a desired optically active carboxylic acid or an ester thereof.

The present invention is now illustrated in greater detail with reference to the following examples, but it should be understood that the present invention is not construed as being limited thereto. All the parts, percents, and ratios are by weight unless otherwise specified.

Analytical instruments used in these examples are shown below.

| High-Performance Liquid Chromatography: | |
| --- | --- |
| | Hitachi L-6000 (manufactured by Hitachi, Ltd.) |
| $^1$H-NMR: | Model AM-400 (400 MH) (manufactured by Bruker Inc.) |
| IR: | Model IR-810 (manufactured by Nippon Bunko Kogyo K.K.) |
| Optical Rotation: | Model DIP-4 (manufactured by Nippon Bunko Kogyo K.K.) |
| Melting Point: | Micro melting point measuring apparatus (manufactured by Yanagimoto Seisakusho K.K.) |

PREPARATION EXAMPLE 1

Synthesis of 2-Acetylamino-3-nitrotoluene (4)

In a 1 l three-necked flask equipped with a stirrer, an Allihn condenser, and a dropping funnel was charged 650 ml (6.9 mole) of acetic anhydride, and 107 g (107 ml, 1 mole) of o-toluidine (2) was slowly added through the dropping funnel. After the dropwise addition, the reaction mixture was cooled to 12° to 13° C., and 126 ml (2 mole) of 70% nitric acid was slowly added thereto while maintaining this temperature. As the reaction proceeded, acetotoluide was re-dissolved and re-precipitated, the solution turned dark red, and there was separated a nitro compound. The solution was poured into 3 l of ice-water while stirring.

Milky yellow 2-acetylamino-3-nitrotoluene (4) and its isomer, 2-acetylamino-5-nitrotoluene, were thus precipitated, which were then collected in a Buchner funnel. The collected precipitates were washed four times with 500 ml of ice-water and dried by suction by means of an aspirator to obtain a mixture of 2-acetylamino-3-nitrotoluene (4) and 2-acetylamino5-nitrotoluene having a melting point of 142.2° to 143° C. and an 81% yield.

PREPARATION EXAMPLE 2

Synthesis of 2-Amino-3-nitrotoluene (5)

The wet mixture of 2-acetylamino-3-nitrotoluene (4) and 2-acetylamino-5-nitrotoluene as obtained in Preparation Example 1 was placed in a steam distillation apparatus, and 300 ml of concentrated hydrochloric acid was added thereto. Immediately on heating and boiling, the mixture was hydrolyzed. The boiling was continued until 36 l of a distillate was collected. On cooling the distillate, there was obtained 2-amino-3-nitrotoluene (5) as an orange needle-like crystal having a melting point of 92.8° to 93.2° C. and a 46% yield.

PREPARATION EXAMPLE 3

Synthesis of 2-Iodo-3-nitrotoluene (6)

In a 500 ml three-necked flask was charged 110 g (0.72 mole) of 2-amino-3-nitrotoluene (5) as obtained in Preparation Example 2, and 260 ml of concentrated sulfuric acid was added thereto, followed by stirring at 0° C. To the solution was added 74.8 g (1.08 mole) of sodium nitrite over 45 minutes, and the solution was stirred at 0° C. for 4 hours, whereby the solution became a dark brown suspension.

The reaction mixture was poured into 3 l of ice-water, and 1 l of an aqueous 53% potassium iodide was added thereto. After stirring at 80° C. for 10 hours, the reaction mixture was treated with 100 g of sodium hydrogensulfite. A supernatant was removed, and insoluble matters were extracted thrice with 500 ml of dichloromethane. An organic layer was neutralized and washed with a saturated sodium hydrogencarbonate aqueous solution, washed with distilled water, and then dried over anhydrous sodium sulfate. The solvent was removed by distillation under reduced pressure to obtain a yellowish brown crude crystal. Recrystallization of the crude crystal from 150 ml of 99% ethanol gave 2-iodo-3-nitrotoluene (6) as a pale yellow crystal having a melting point of 64.8° to 65.2° C. and an 84% yield (inclusive of secondary crystals recovered from the filtrate after recrystallization).

PREPARATION EXAMPLE 4

Synthesis of 6,6'-Dimethyl-2,2'-dinitro-1,1'-biphenyl (7)

In an eggplant flask having a ground-in stopper and equipped with a condenser were charged 2-iodo-3-nitrotoluene (6) as obtained in Preparation Example 3 and an equivalent weight of a copper powder, and the contents were stirred in an oil bath at 200° C. for 10 hours. The mixture was extracted with benzene by means of a Soxhlet extractor. The solvent was removed from the extract by distillation under reduced pressure, and the resulting crude crystal was recrystallized from 99% ethanol to obtain 6,6'-dimethyl-2,2'-dinitro-1,1'-biphenyl (7) as a black needle-like crystal having a melting point of 107.4° to 108.3° C. and a 73% yield.

PREPARATION EXAMPLE 5

Synthesis of 6,6'-Dimethyl-2,2'-diamino-1,1'-bichenyl (8)

The atmosphere of a 500 ml eggplant flask equipped with a three-way cock at the top and an Allihn condenser was dried under reduced pressure and displaced with nitrogen. In the flask was charged 13.6 g (50 mmole) of 6,6'-dimethyl-2,2'-dinitro-1,1'-biphenyl (7) as obtained in Preparation Example 4 and dissolved in 120 ml of warm 99% ethanol having been previously displaced with nitrogen, followed by stirring. To the mixture was added 35 ml (0.7 mole) of hydrazine hydrate having been displaced with nitrogen. A suspension of 3 ml of a Raney nickel W2 type catalyst in ethanol was slowly added thereto by means of a syringe while maintaining the activity. Thereafter, the mixture was heated at reflux in an oil bath until the whole of the hydrazine was consumed.

After completion of the reaction, the catalyst was removed by filtration through Celite, and the solvent was removed from the filtrate by distillation under reduced pressure to obtain 6,6'-dimethyl-2,2'-diamino- 1,1'-biphenyl (8) as a pale brown crystal having a melting point of 132.5° to 133.8° C. and a 96.3% yield.

PREPARATION EXAMPLE 6

Synthesis of 6,6'-Dimethyl-2,2'-dibromo-1,1'-biphenyl (9)

In 2.8 ml (24 mmole) of 47% hydrobromic acid was dissolved 1.0 g (4.76 mmole) of 6,6'-dimethyl-2,2'-diamino-1,1'-biphenyl (8) as obtained in Preparation Example 5, and the solution was cooled to 0° C. in an ice bath. A solution of 655 mg of sodium nitrite in 1.2 ml of water was slowly added to the solution over a period of 10 minutes, followed by stirring at −5° to −3° C. for 2.5 hours. The solution was slowly added to a refluxing solution of 73.7 mg (5 mmole) of cuprous bromide in 1.5 ml (13 mmole) of 47% hydrobromic acid, and the mixture was refluxed for 2.5 hours. To the reaction mixture were added 30 ml of dichloromethane and 20 ml of distilled water to thereby thoroughly extract an organic layer. The extract was washed successively with 10 ml of a saturated sodium hydrogencarbonate aqueous solution, 10 ml of distilled water, and 10 ml of a saturated potassium nitrate aqueous solution and dried over anhydrous sodium sulfate. The solvent was removed by distillation under reduced pressure to obtain a black oily crude crystal which was then purified twice by means of column chromatography according to the following conditions to give 6,6'-dimethyl-2,2'-dibromo-1,1'-biphenyl (9) as a white crystal having a melting point of 90.0° to 92.3° C. and a 47% yield.

| 1st Time: | |
| --- | --- |
| Column: | Silica gel (200 mesh pass) 29 g; diameter: 18 mm |
| Solvent: | 1:10 (by volume) mixture of benzene and hexane |
| Recovered Fraction: | 50 to 210 ml |
| TLC: | Rf = 0.87; 100% benzene |
| Crystal Appearance: | Reddish orange crystal |
| Column Recovery: | 87% |
| 2nd Time: | |
| Column: | Silica gel (200 mesh pass) 15 g; diameter: 18 mm |
| Solvent: | 1:20 (by volume) mixture of benzene and hexane |
| Recovered Fraction: | 50 to 90 ml |
| TLC: | Rf = 0.52; 5% benzene-hexane |
| Crystal Appearance: | White crystal |
| Column Recovery: | 58% |

Purification may be accomplished through one column chromatography by controlling the column volume, the solvent concentration, and the like.

Melting Point: 87° to 93° C.

$^1$H—NMR (δppm; CDCl$_3$): 2.0 (s, —CH$_3$, 6H), 7.0–7.5 (m,-Ph, 6H)

MS (M/e): 338, 340, 342

PREPARATION EXAMPLE 7

Synthesis of 2,2'-Bis(dicyclohexylphosphinyl)-6,6'-dimethyl-1,1'-biphenyl (11)

In a 100 ml two-necked eggplant flask equipped with a Dimroth condenser whose atmosphere had been dried and replaced with nitrogen were charged 1.00 g (2.94 mmole) of 6,6'-dimethyl-2,2'-dibromo-1,1'-biphenyl (9) as obtained in Preparation Example 6 and 10 ml of dry tetrahydrofuran, followed by stirring at room temperature to thoroughly dissolve. The flask was cooled to a limit (−78° C.) by using solid carbon dioxide-methanol, and 13 ml (22.1 mmole) of t-butyllithium was slowly added dropwise to the mixture at that temperature over a period of 2 hours.

Thereafter, the mixture was gradually warmed and allowed to react for at least 4 hours while maintaining the temperature at about −45° C. The mixture was again cooled to −78° C., and 5.50 g (22.2 mmole) of dicyclohexylphosphinic chloride (10) thoroughly dissolved in 20 ml of dry tetrahydrofuran was added dropwise thereto, followed by stirring overnight. During the stirring, the temperature was allowed to elevate with a Dewar vessel being fixed. After the reaction was continued until the mixture was warmed to room temperature by spontaneous temperature elevation, the mixture was heated at reflux for 3 hours. The solvent was removed by distillation under reduced pressure, and the residue was completely dissolved in 20 ml of toluene. A white insoluble matter thus formed was removed by filtration.

The resulting toluene solution was washed successively twice with distilled water, thrice with a 2N sodium hydroxide aqueous solution, and once with distilled water. An adequate amount of potassium carbonate was added thereto for drying. The potassium carbonate was separated by filtration through a cotton plug, and the solvent was removed by distillation under reduced pressure. To the residue was added about 10 ml of acetone, and the solution was sufficiently stirred while lightly warming with a drier. A thus precipitated white crystal was collected by filtration to obtain the novel compound of the present invention, 2,2'-bis(dicyclohexylphosphinyl)-6,6'-dimethyl-1,1'-biphenyl (11) and a 39.3% yield.

Melting Point: 270–277° C.

$^1$H—NMR (δ ppm, CCl$_4$): 0.8–2.2 (m, —CH$_3$, —Cy, 50H), 7.0–7.4 (m, —Ph, 6H)

$^{31}$P—NMR (δ ppm, CCl$_4$) (external standard: H$_3$PO$_4$): 44.4

MS (M/e): 606 (M$^+$)

IR: 2940 cm$^{-1}$ νCH$_3$ 2860 cm$^{-1}$ νCH$_2$ (cyclo) 1450 cm$^{-1}$ νP—PH 1180 cm$^{-1}$ νP=O

PREPARATION EXAMPLE 8

Optical Resolution of 2,2'-Bis(dicyclohexylphosphinyl-6,6'-dimethyl-1,1'-biphenyl (12)

In a 100 ml two-necked eggplant flask equipped with an Allihn condenser was charged 692.5 mg (1.143 mmole) of racemic 2,2'-bis(dicyclohexylphosphinyl)-6,6'-dimethyl-1,1'-biphenyl (11) as obtained in Preparation Example 7, and 50 ml of ethyl acetate and 2.5 ml of chloroform were added thereto, followed by heat-refluxing to dissolve. The amounts of ethyl acetate and chloroform to be added were adjusted so that the resulting solution could become substantially clear.

Then, 409.5 mg (1.143 mmole) of (−)-dibenzoyltartaric acid dissolved in hot ethyl acetate was charged in the flask immediately after being taken out of the oil bath. After stirring for several seconds, the solution was allowed to stand overnight (a crystal began to precipitate in about 30 seconds), and the thus precipitated crystal was collected by filtration.

Optical rotations of both of a sparingly soluble diastereomer (salt of opposite signs, i.e., (+)(−)-salt) and an easily soluble diastereomer (salt of same signs, i.e., (−)(−)-salt) were measured. If the measured optical rotations were not appreciably different from the values shown below, the product was neutralized as follows to obtain an optically active diphosphine oxide. The crystal was thoroughly dissolved in about 40 ml of a 2N sodium hydroxide aqueous solution and about 40 ml of toluene with stirring, followed by liquid-liquid separation. The sodium hydroxide layer was extracted twice or thrice with about 20 ml of toluene.

An adequate amount of potassium carbonate was added to the toluene layer for drying. After filtration through a cotton plug, the solvent was removed by distillation under reduced pressure to obtain (+)- or (−)-2,2'-bis(dicyclohexylphosphinyl)-6,6'-dimethyl-1,1'-biphenyl (12).

The resulting optically active compound (12) was repeatedly recrystallized using ethyl acetate and chloroform until the specific rotatory power of the crystal was no more varied.

| (+)-Isomer | $[\alpha]_D$ | +72.7° |
|---|---|---|
|  | $[\alpha]_{435}$ | +155.0° |
| (−)-Isomer | $[\alpha]_D$ | −75.3° |
|  | $[\alpha]_{435}$ | −155.0° |

PREPARATION EXAMPLE 9

Synthesis of Optically Active 2,2'-Bis(dicyclohexylphosphino)-6,6'-dimethyl-1,1'-biphenyl (BICHEP)

In a 5 ml vessel was placed 215 mg (0.355 mmole) of the (−)-enantiomer of the optically active diphosphine oxide (12) as obtained in Preparation Example 8 ($[\alpha]_D$ −75.3°; optical purity: 98.7%), and the atmosphere was displaced with argon. Three milliliters of anhydrous xylene was added thereto as a solvent, and the mixture was heated until almost a half of the (−)-diphosphine oxide dissolved. During the heating, care was taken so that the liquid temperature did not exceed 100° C. in order to prevent racemization by heating. The container was then allowed to cool to room temperature, and 0.43 ml (4.17 mmole) of trichlorosilane was injected therein using a previously ice-cooled syringe. A Schlenk tube containing trichlorosilane to be added had to be kept under ice-cooling. After injection, the content was sufficiently stirred and cooled in an ice bath for several minutes. Upon addition of 0.52 ml (3.73 mmole) of triethylamine, the solution turned yellow and began to solidify. The mixture was again stirred to form a uniform gel. The gel was further allowed to react in an oil bath at 120° C. for 4 hours and then at 130° C. for 2 hours. After allowing to cool to room temperature, several milliliters of xylene was added thereto in a nitrogen atmosphere, and the content was transferred to a Schlenk's tube in a nitrogen atmosphere by using a simplified gloved box.

Five milliliters of a 30% sodium hydroxide aqueous solution having been displaced with nitrogen was added to the reaction mixture to dissolve all the solid products, and 5 ml of methylene chloride was further added thereto, followed by refluxing at 60° C. for 2 hours. An upper organic layer was separated with a syringe, and an aqueous layer was extracted twice with 5 ml of methylene chloride. The resulting organic layer was dried over an adequate amount of sodium sulfate, and the solvent was removed by distillation in vacuo.

A thus obtained crude product was passed through a short column (SiO$_2$, Merck Kieselgel 60; diameter: 18 mm; height: 5 cm) and eluted with benzene to remove the unreacted diphosphine oxide (12). The eluent was distilled in vacuo to remove the solvent to obtain 162 mg (percent yield: 61.9%) of (−)-BICHEP as a white solid.

$[\alpha]_D^{20}$ −105.9° (c=0.816, CH$_2$Cl$_2$)

The thus obtained optically active BICHEP was repeatedly recrystallized to preferentially crystallize a one-sided enantiomer to increase its optical purity. The recrystallization operation was repeated until the specific rotatory power of the crystal no more changed. The specific rotatory power of the resulting crystal was taken as a specific rotatory power of an enantiomer of BICHEP having a optical purity of 100%. The procedure taken here was as follows.

The (+)-enantiomer of the optically active diphosphine oxide (12) obtained by reduction was charged in a Schlenk tube equipped with a stirrer in a nitrogen atmosphere. Warm ethyl acetate which had been displaced with nitrogen was added thereto in small portions as a solvent with stirring. At the point when all the solid matter dissolved, the stirring was ceased, and the solution was allowed to cool to room temperature and then cooled in a refrigerator (−3° C.) for about 30 minutes, whereby a semi-transparent crystal of BICHEP was obtained. The solvent was removed by using a syringe in a nitrogen atmosphere, and the crystal was distilled in vacuo to remove any residual solvent and then dried. Specific rotatory power of the resulting crystal was measured with a polarimeter using methylene chloride as a solvent.

On the other hand, an optically pure crystal of (−)BICHEP was obtained in the same manner as described above.

$[\alpha]_D^{32}$ −119.5° (c=0.826, CH$_2$Cl$_2$)

Accordingly, the specific rotatory power of this optically active compound having an optical purity of 100% was found to be +119.7° or −119.7° (the decimal fraction was within the error of the polarimeter).

Properties of BICHEP

Melting Point: 178°–182° C.
$^1$H—NMR (δ ppm, CCl$_4$): 0.8-2.2 (m, —CH$_3$, —Cy, 50H) 7.1-73 (m, —Ph, 6H)
$^{31}$—NMR (δ ppm, CD$_2$Cl$_2$, external standard: 85% H$_3$PO$_4$): −9.67
MS: 574 (M+)

EXAMPLE 1

Synthesis of (2,2'-Bis(dicyclohexylphosphino)-6,6'-dimethyl-1,1-biphenyl) Ruthenium Diacetate Comolex [Ru(BICHEP)](OAc)$_2$ In a Schlenk tube whose atmosphere had been displaced with nitrogen were charged 94.6 mg (0.165 mmole) of BICHEP as obtained in Preparation Example 9 and 44.3 mg (0.151 mmole/Ru) of [Ru(cycloocta-1,5-diene)Cl$_2$]$_n$, and 20 ml of toluene was added thereto. To the mixture was added 22.9 mg (0.226 mmole) of triethylamine in a nitrogen atmosphere, whereby the reaction system became a brown suspension. The suspension was heat-refluxed for 12 hours, whereby the reaction system became a deep brown solution. The solution was filtered through Celite, and the solvent was removed by distillation. To a greenish brown solid thus obtained was added a suspension of 66.3 mg (0.808 mmole) of sodium acetate in t-butanol. The resulting reddish brown suspension was heat-refluxed for 16 hours, and the resulting orange suspension was filtered through Celite. The solvent of the resulting brown solution was removed by distillation. The resulting brown solid was recrystallized from a mixed solvent of 0.4 ml of toluene and 1.0 ml of hexane and vacuum dried to obtain 35.3 mg (0.0444 mmole, percent yield: 29%) of a yellow crystal.

NMR Data $^1$H—NMR ($\delta$ ppm, CDCl$_3$): 0.25-2.85 (m, 44H, C$_6$H$_{11}$—), 1.68, 2.02, 2.18, 2.32 (s, 12H, Me—), 6.65-7.70 (m, 6H, aromatic)

—$^C$—NMR ($\delta$ ppm, CDCl$_3$): 14.1-42.7 (m, Me—, C$_6$H$_{11}$—), 122.9-149.8 (m, aromatic), 178.2, 184.0 (s, carbonyl)

$^{31}$P—NMR ($\delta$ ppm, CDCl$_3$): 61.4, 61.8 (s) (external standard: 85% H$_3$PO$_4$)

EXAMPLE 2

Synthesis of p-Cymene (2,2'-Bis(dicyclohexylphosphino)-6,6'-dimethyl-1,1'-biphenyl) Ruthenium Diiodide Complex [Ru(BICHEP)(p-cymene)I]I In a Schlenk tube whose atmosphere had been displaced with nitrogen was charged 315.7 mg (0.549 mmole) of BICHEP as obtained in Preparation Example 9 and dissolved in a mixed solvent of 8 ml of methylene chloride and 5 ml of ethanol. In another Schlenk tube was charged 268.5 mg (0.274 mmole) of [Ru(p-cymeme)I$_2$]$_2$ and, after the atmosphere was displaced with nitrogen, dissolved in a mixed solvent of 5 ml of methylene chloride and 10 ml of ethanol to form a deep purple solution. The deep purple solution was transferred to the above-prepared BICHEP solution by means of a catheter in a nitrogen atmosphere. At this time, the reaction system showed no appreciable change. The mixture was heat-refluxed for 4 hours, and the solvent was removed by distillation. The residual solid was recrystallized from a mixed solvent of 8 ml of methylene chloride and 2 ml of diethyl ether and vacuum dried to obtain 328.8 mg (0.309 mmole, yield: 56.3%) of a brownish purple crystal.

NMR Data $^1$H—NMR ($\delta$ ppm, CDCl$_3$): 0.37-2.30 (m, 44H, C$_6$H$_{11}$—), 1.27 (d, 6H, isopropyl-Me), 2.04, 2.10 (s, 6H, BICHEP—Me), 2.35 (s, 3H, Me), 3.00 (m, 1H, CH), 3.00-3.47 (br, 4H, arene), 5.32-5.55, 7.28-7.53 (m, 6H, aromatic)

$^{31}$P—NMR (6 ppm, CDCl$_3$): 69.4, 77.8 (br) (external standard: 85% H$_3$PO$_4$)

REFERENCE EXAMPLE 1

Asymmetric Hydrogenation

In a 100 ml glass-made pressure vessel which had been purged with nitrogen were charged successively with 79.3 mg (0.1 mmole) of the [Ru((R)-BICHEP)](OAc)$_2$ complex as obtained in Example 1, 30 ml of ethanol, and 2.33 g (10 mmole) of ethyl (Z)-α-acetamidocinnamate. The mixture was subjected to hydrogenation at 25° C. under a hydrogen pressure of 5 kg/cm$^2$ for 5 hours. The reaction mixture was subjected to silica gel column chromatography to remove the catalyst. The residue was determined by $^1$H—NMR and optical rotation and found to be ethyl 2-acetylamino-3-phenylpropionate having an optical purity of 91% ee.

REFERENCE EXAMPLE 2

Asymmetric Hydrogenation

In a 100 ml glass-made pressure vessel which had been purged with nitrogen were charged successively with 93.6 mg (0.1 mmole) of the [Ru(S)-BICHEP)(p-cymene)I]I complex as obtained in Example 2, 30 ml of ethanol, and 2.33 g (10 mmole) of ethyl (Z)-α-acetamidocinnamate. The mixture was subjected to hydrogenation at room temperature under a hydrogen pressure of 5 kg/cm$^2$ for 45 hours. The reaction mixture was treated in the same manner as in Reference Example 1 to obtain ethyl 2-acetylamino-3-phenylpropionate having an optical purity of 85% ee.

As described above, the ruthenium-optically active phosphine complex according to the present invention can catalyze asymmetric syntheses, such as asymmetric hydrogenation, asymmetric isomerization, and asymmetric silylation, exhibiting excellent catalytic activity and providing high optical purity.

While the invention has been described in detail and with reference to specific embodiments thereof, it will be apparent to one skilled in the art that various changes and modifications can be made therein without departing from the spirit and scope thereof.

What is claimed is:

1. A ruthenium-optically active phosphine complex having, as a ligand, BICHEP which means 2,2'-bis(dicyclo-hexylphosphino)-6,6'-dimethyl-1,1'-biphenyl represented by formula (I):

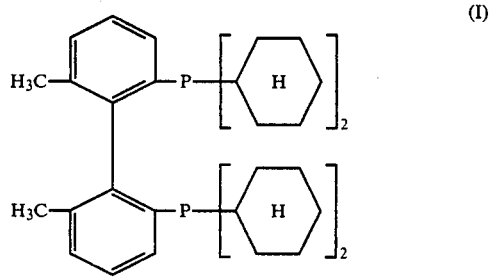

2. A ruthenium-optically active phosphine complex as in claim 1, represented by formula (II):

$[Ru(BICHEP)](OCOR^0)_2$         (II)

wherein R$^0$ represents a lower alkyl group or a substituted or unsubstituted aryl group.

3. A ruthenium-optically active phosphine complex as in claim 1, represented by formula (III):

$[RuXA(BICHEP)]X'$         (III)

X and X' simultaneously represent the same halogen atom; and A represents a substituted or unsubstituted phenyl group.

4. A ruthenium-optically active phosphine complex as in claim 1, represented by formula (IV):

$[Ru_2Cl_4(BICHEP)_2]R^{00}$         (IV)

wherein R$^{00}$ represents a tertiary amine.

5. A ruthenium-optically active phosphine complex as in claim 2, represented by [Ru(BICHEP)](OAc)$_2$, wherein Ac means an acetyl group.

6. A ruthenium-optically active phosphine complex as in claim 3, represented by [Ru(BICHEP)(p-cymene)I]I.

* * * * *